United States Patent [19]

Louderback et al.

[11] Patent Number: 4,579,824

[45] Date of Patent: Apr. 1, 1986

[54] HEMATOLOGY CONTROL

[76] Inventors: Allan L. Louderback, 9661 Longden Ave., Temple City, Calif. 91780; Paul Szatkowski, 24 Winthrop Rd., Bethel, Conn. 06801

[21] Appl. No.: 495,629

[22] Filed: May 18, 1983

[51] Int. Cl.⁴ .................... G01N 31/00; G01N 33/00
[52] U.S. Cl. .......................................... 436/10; 436/8; 436/17; 436/63; 252/408.1
[58] Field of Search ............... 436/10, 63, 178; 252/408.1

[56] References Cited

U.S. PATENT DOCUMENTS

| 3,558,522 | 1/1971 | Louderback et al. | 252/408 |
|---|---|---|---|
| 3,574,137 | 4/1971 | Descasperis | 252/408 |
| 3,640,896 | 2/1972 | De Casperis | 252/408 |
| 3,715,427 | 2/1973 | Hirata | 436/17 X |
| 3,873,467 | 3/1975 | Hunt | 436/17 X |
| 3,962,125 | 6/1976 | Armstrong | 436/10 X |
| 3,973,913 | 8/1976 | Louderback | 23/230 |
| 4,102,810 | 7/1978 | Armstrong | 436/10 X |
| 4,126,575 | 11/1978 | Louderback | 436/11 |
| 4,160,644 | 7/1979 | Ryan | 436/10 |
| 4,199,471 | 4/1980 | Louderback et al. | 436/10 |
| 4,264,470 | 4/1981 | Chastain, Jr. et al. | 436/17 |
| 4,299,726 | 11/1981 | Crews | 436/10 |
| 4,324,686 | 4/1982 | Mundschenk | 436/10 |
| 4,324,687 | 4/1982 | Louderback et al. | 436/10 X |
| 4,346,018 | 8/1982 | Carter et al. | 436/17 |
| 4,379,847 | 4/1983 | Fruitstone | 436/18 X |
| 4,412,004 | 10/1983 | Ornstein et al. | 436/16 X |
| 4,489,162 | 12/1984 | Hawkins | 436/10 |

OTHER PUBLICATIONS

Carpenter, "Immunology and Serology", W. B. Saunders Company, Second Edition, 1965, at p. 410.

Primary Examiner—Teddy S. Gron
Assistant Examiner—Catherine S. Kilby

[57] ABSTRACT

A hematology control is disclosed which is useful for clinical hematology procedures and, in particular, mean corpuscular volume (MCV) determinations. The hematology control comprises an aqueous suspension of red blood cells in which varying levels of MCV are provided by applying to the red cell component, after light treatment with aldehyde, an osmotic pressure that is directly proportional to the desired red blood cell size.

14 Claims, No Drawings

HEMATOLOGY CONTROL

BACKGROUND OF THE INVENTION

This invention relates to a hematology control which is useful for clinical hematology procedures and, particularly, mean corpuscular volume (MCV) determinations.

Hematology control products are widely used as quality control materials to monitor determination of blood cell values in various established clinical hematology procedures. Specific blood cell measurements that are made by these procedures are white blood cell counts (WBC), red blood cell counts (RBC), hemoglobin content (Hgb), hematocrit (Hct) or packed cell volume, mean corpuscular volume (MCV), mean corpuscular hemoglobin (MCH) and mean corpuscular hemoglobin concentration (MCHC). The function of the hematology control product is to provide a means of ascertaining the accuracy and precision of these specific blood cell measurements in which the control is used in the same manner as the patient's specimen in the analysis procedure.

Hematology control products for the above clinical hematology procedures are well known. In these prior art products, human or animal cells having known values are often employed in aqueous suspension such as saline and buffered saline, or synthetic particles such as latex or other inert particles are used to simulate human blood cells, usually the white cells, in the suspension. Cells for these hematology control products also have been known to be stabilized such as by fixation with aldehydes or tannic acid. Thus, U.S. Pat. Nos. 3,574,137 and 3,640,896 disclose hematology controls comprising an aqueous suspension of fresh human red blood cells and tanned fowl red blood cells such as turkey or chicken cells. The fowl red blood cells are stringently fixed with tannic acid and glutaraldehyde and are used in the composition to simulate human white blood cells for white blood cell counting purposes. After fixation, the cells are suspended in Alsever's Solution. U.S. Pat. No. 3,558,522 describes a hematology control comprising washed red blood cells and small latex particles (to simulate white blood cells) in an aqueous suspension of albumin. Alsever's Solution is used for washing the red blood cell component of the hematology control.

None of the above prior art hematology control products are readily adaptable to provide varying levels of MCV such as would be desirable for control purposes in the assay of patient specimens having wide fluctuations in this parameter. Instead, it has been customary practice in the hematology field to pre-select cells of the desired size for incorporation in the hematology control products.

A close relationship exists in various of the aforesaid hematology measurements. Thus, the red blood cells (RBC) or erythrocytes contain hemoglobin (Hgb) which is the essential oxygen carrier of the blood. The hematocrit (Hct) test measures the relative volume of the cells and plasma in the blood. Normally, the Hgb level is about 15 gm/dl of blood, with women showing values slightly lower than men. The average normal value of packed red cells (Hct) is about 47% of the blood volume in men and about 42% in women. From the RBC, Hgb and Hct values, certain important morphological characteristics of the blood can be defined, namely:

Mean Corpuscular Volume (MCV),
Mean Corpuscular Hemoglobin (MCH),
Mean Corpuscular Hemoglobin Concentration (MCHC) and Color Index (C.I.).

The Hct also can be derived mathematically from an averaged value for the MCV. Anemias with $MCV < 80\mu^3$ are termed microcytic; with $MCV > 94\mu^3$, macrocytic. Values of MCH, MCHC and C.I. of $<27$ $\mu\mu$gm, $<32$ gm/dl and $<0.9$, respectively, are indicative of Hgb deficiency, or hypochromia. Anemias with MCH and C.I. of $>32$ $\mu\mu$gm and $>1.1$, respectively, are termed macrocytic; but because of the greater cell size, the MCHC remains normal. These various indicies aid in determining the nature of an anemia in a patient.

It is seen from the above that the preparation of a hematology control product with varying MCV levels to simulate normal as well as abnormally high or low would have significant use in the hematology field.

Accordingly, it is a primary object of the invention to provide a hematology control product and a method for its preparation in which the MCV can be readily adjusted to varying levels from abnormally low to abnormally high.

DESCRIPTION OF THE INVENTION

In accordance with the present invention, a hematology control comprising an aqueous suspension of human or other mammalian red blood cells for control of MCV and related hematology assays is provided in which, after light treatment with aldehyde, the red blood cell component is subjected to an osmotic pressure that is directly proportional to the desired cell size. By this method, varying levels of MCV of from about 70 to about $105\mu^3$ can be readily obtained from any batch of red blood cells without the need to preselect cells of the desired size for use in the hematology control as heretofore commonly practiced. Hematology controls with MCV values preferably ranging from about 75 to about $95\mu^3$ are readily obtained from any batch of red blood cells according to this method by varying the osmotic pressure on the red blood cells, after they have been lightly treated with aldehyde, to a corresponding range of from about 115 to about 275 mOsms. Reduced MCV values are obtained by further proportionate reduction in the osmotic pressure, while increased MCV values are obtained by further proportionate increase in the osmotic pressure.

In order to crush normal red blood cells down to a reduced mean cell volume, it was initially believed to be desirable to increase the pressure on these cells. However, it was surprisingly and unexpectedly found that reducing, instead of increasing, the osmotic pressure provided a desired reduction in mean cell volume when carried out after the red blood cells were lightly treated with aldehyde. Thus, in the preferred MCV range of 75 to $95\mu^3$, the lower value of 75 is obtained by application of the lower osmotic pressure of about 115 mOsms while the higher value of 95 is obtained by application of the higher osmotic pressure of about 275 mOsms. The MCV mid value of 85 is obtained by application of the intermediate osmotic pressure of about 150 mOsms.

Red blood cells have an outer semipermeable membrane and are subject to osmotic pressure. The osmotic pressure on the cells in solution is dependent upon the molar concentration and the temperature of the solution. The molarity of the solution is defined as the concentration of the solution as a ratio of solute to solution, which is a weight to volume relationship. Thus, a change in the concentration of sodium chloride in the solution will cause a change in the osmotic pressure upon the cells in the solution. Normal whole blood has an osmotic pressure which corresponds to that of a 0.9% solution of sodium chloride. A sodium chloride solution of this concentration is said to be iso-osmotic with blood. The term "isotonic", which means equal tone, is commonly used interchangeably with iso-osmotic. Solutions with a lower osmotic pressure than provided with 0.9% sodium chloride are referred to as hypo-osmotic, while solutions having greater osmotic pressure are termed hyper-osmotic.

Osmotic pressure measurements are made only with comparatively greater difficulty and generally are not as accurate as other colligative properties of solutions. For this reason, the freezing point depression, which is readily measured with reasonably accuracy, is most frequently used in determining the tonicity of a solution. Thus, the osmotic pressure changes caused by changes in molar concentration are conveniently determined by osmometers which measure the freezing points of liquids. The more salt that is dissolved in a liquid, the lower will be the freezing point. For dilute solutions, the freezing point is linear with the number of dissolved particles. By common usage, osmolality is directly proportional to freezing point temperature. That is:

one mOsm/Kg=freezing point lowering of 1.858 millidegrees C.

wherein mOsm=millosmol.

A milliosmol (mOsm) is equal to 1/1000 of an osmol or 17 mm Hg pressure. Thus, 100 mOsms equal 1700 mm Hg pressure or 2.2368 atmospheres pressure (that is, b 1700/760=2.2368).

The osmotic pressure range of normal human blood serum according to the recognized experts in the field of hematology is 290-310 mOsms (Todd-Sanford Clinical Diagnosis by Laboratory methods, XIII th ed., 1963, Edited by Davidsohn and Wells, W. B. Saunders Co., Philadelphia), or 278-305 mOsms (Henry et al., Clinical Chemistry Principles and Technics, 2nd ed., 1974, Harper & Row, New York).

Using the value 300 mOsm as a reasonable average of the above two ranges as reported in the leading treatises in the field of the clinical chemistry, normal human serum is seen to have an osmotic pressure of about 6.71 atmospheres based on the foregoing formulas.

Blood cells that are stored for in vitro use are commonly preserved in a solution known as Alsever's Solution. This solution is conventionally defined to have the following composition as reported by Kwapinski, "Methodology of Immunochemical and Immunological Research", Wiley-Interscience, 1972, at page 483:

2.05 g dextrose,
0.8 g trisodium citrate (dihydrate), and
0.42 g sodium chloride in 100 ml distilled water. The solution is then adjusted to pH 6.1 with 10% citric acid and sterilized by filtration. The author further suggests that penicillin and streptomycin can be added to give a final concentration of about 50 units and 100 μg/ml, respectively.

In another leading text, Carpenter, "Immunology and Serology", W. B. Saunders Co., Second Edition, 1965, at page 410, Alsever's Solution is reported to consist of:

Glucose 2.05%,
Sodium Citrate 0.80%,
Sodium Chloride 0.42%, and
Citric Acid 0.055%.

A modified Alsever's Solution is described by Davidsohn and Wells, "Todd-Sanford, Clinical Diagnosis by Laboratory Methods", 13th ed., 1963, at page 280, as follows:

2.05 g dextrose,
0.05 g citric acid,
0.8 g sodium citrate, and
0.45 g sodium chloride dissolved in 100 ml water with pH being 6.1. At page 934 in the same text, a composition is shown which is identical to the foregoing composition described by Carpenter. Similarly, the same composition for Alsever's Solution is reported by Lewis and Coster, "Quality Control in Haematology", Academic Press, 1975, at page 85.

In U.S. Pat. No. 3,558,522, which relates to a hematology control containing red blood cells, and in U.S. Pat. No. 3,973,913, which relates to a blood gas control containing aldehyde treated red blood cells, the cells are also treated with Alsever's Solution having the same 0.42% sodium chloride concentration reported in the above literature (namely 4.2 grams per liter of solution in the former patent or 12.6 grams per three liters of solution in the latter patent).

As distinguished from all of the foregoing, a modified Alsever's Solution is applied to the red blood cells by the present invention in its preferred embodiment to reduce the osmotic pressure by correspondingly reducing the molar concentration of the sodium chloride in the solution. Thus, in the preferred MCV range of 75 to 95μ$^3$, the sodium chloride is reduced to the range of 0.01% to 0.21% which is significantly and substantially lower than the 0.42% or 0.45% reported in the prior art. The other conventional components of Alsever's Solution, namely dextrose (glucose), citric acid and sodium citrate also can be employed herein. However, instead of providing a solution pH of 6.1 as described in the prior art, the pH is adjusted herein to a range of from about 6.8 to about 7.4, and preferably about 7.2. This pH level can be obtained by suitable adjustment of the amount of citric acid used in the solution. While conventional levels of dextrose are used in the present hematology control containing the relatively high MCV values (e.g. 95), sucrose is preferably used in the corresponding controls containing the lower MCV values (e.g. 75-85). Since sucrose has a molecular weight twice that of dextrose (and has two saccharide units), the amount of sucrose used is about ½ the amount of dextrose used. The use of sucrose also reduces the molar concentration as follows:

Dextrose Mol. wt. = 180

Therefore, $\frac{20.5 \text{ g/L}}{180}$ = 0.113 molal solution

Sucrose Mol. wt. = 342

Therefore, $\frac{10.0 \text{ g/L}}{342}$ = 0.029 molal solution

Small but effective amounts of antibacterials such as, e.g., Neomycin and Chloramphenicol, and fungicides such as, e.g., Fungizone ® (Amphotericin B), also are preferably incorporated in the modified Alsever's Solution for their known preservative effects.

The red blood cells are preferably lightly treated with aldehyde such as formaldehyde or glutaraldehyde in the general manner disclosed in U.S. Pat. No.

3,973,913. The disclosure of said patent concerning the light treatment of the red blood cells with aldehyde is incorporated herein by reference. This light treatment is conveniently carried out by subjecting the cells to a dilute solution of formaldehyde, e.g., having proportions of about 40 ml of 37% formaldehyde and about 500 ml of 0.9% saline. The cells are preferably suspended in the formaldehyde/saline solution for about two hours at about 18°–28° C. Following this treatment, the cells are washed in saline to remove the residual formaldehyde. At this point, the cells are still plastic since they have not been rigorously treated with the aldehyde to become hard. They retain this plasticity for up to about five days after the aldehyde treatment. Thus, they can be readily molded to another desired MCV by treatment with the aforesaid modified Alsever's Solution preferably within about five days after such contact with the aldehyde.

In addition to the red blood cell component, the hematology control of this invention also contains a simulated human white blood cell component as a preferred embodiment. Avian red blood cells such as turkey, but preferably chicken, cells are employed in this embodiment. These cells should be stringently (rigorously) fixed with aldehyde such as formaldehyde or glutaraldehyde. This fixation can be conveniently carried out by treating the cells with formaldehyde/saline solution as described above except that rigorous rather than light treatment is applied, whereby the cells become hard. Thus, the avian cells are preferably suspended in the formaldehyde/saline solution for about one hour at about 20°–28° C., then for about two hours at about 37° C., and then at ca. 20°–28° C. for another 24 hours. Following this rigorous treatment, the cells are very hard and are washed in saline to remove the residual formaldehyde.

The following more detailed examples will illustrate the invention further although it will be understood that the invention is not limited to these illustrative details.

EXAMPLE 1

Preparation of Modified Alsever's Solution

To three liters of deionized water, the following constituents were added in three MCV test levels and moderately stirred until completely dissolved:

| Constituent | Desired MCV Level ($\mu^3$) | | |
|---|---|---|---|
| | 75 | 85 | 95 |
| Dextrose (Glucose) | 0 | 0 | 61.5 g |
| Sucrose | 30 g | 30 g | 0 |
| Sodium Chloride | 0.3 g | 3.1 g | 6.3 g |
| Citric Acid (1% Solution) | 15.6 ml | 15.6 ml | 15.6 ml |
| Neomycin Sulfate | 330 mg | 330 mg | 330 mg |
| Chloramphenicol | 990 mg | 990 mg | 990 mg |
| Fungizone | 2.0 ml | 2.0 ml | 2.0 ml |
| Sodium Citrate | 24 g | 24 g | 24 g |
| Deionized Water (Total) | 3 L | 3 L | 3 L |

The pH of each of the above three test solutions was about 7.2. The osmotic pressure of these solutions was determined on a commercially available osmometer, namely, the Advanced Instruments Inc. Osmometer (Needham Heights, Mass.) and compared with that of a base solution for control purposes. The base solution consisted of all the constituents common to the above test solutions except the sugars and sodium chloride. The resulting osmotic pressures were as follows:

| Solution | Osmotic Pressure mOsm/Kg Water |
|---|---|
| Base Solution | 85 |
| 75 MCV Solution | 117 |
| 85 MCV Solution | 147 |
| 95 MCV Solution | 271 |

It is seen from this example that the osmotic pressure of all three test solutions (the modified Alsever's Solutions) is less than the average reported value of about 300 mOsm/Kg for normal human blood serum and that the reduction in the osmotic pressure caused by a reduction in the molar concentration provided a directly proportional reduction in MCV. The MCV values are determined on commercially available hematology instruments, namely, Coulter S, Coulter 4/30, and Coulter S Plus electronic hematology instruments.

EXAMPLE 2

Preparation of Hematology Controls

Normal human red blood cells washed in 0.9% saline and then resuspended in 0.9% saline were lightly treated with a solution of formaldehyde and saline followed by treatment with the modified Alsever's Solutions of Example 1, above. The formaldehyde/saline solution consisted of 40 ml of 37% formaldehyde in 500 ml of 0.9% saline. In this example, 375 ml of the washed cells in two liters of 0.9% saline were gently mixed with 540 ml of the formaldehyde/saline solution over a period of about two hours at about 18° to 28° C. The cells were washed free of residual formaldehyde by washing in 0.9% saline and then three aliquots of the treated cells were washed with the different modified Alsever's Solutions to obtain three levels of MCV, namely, 75, 85, and 95$\mu^3$, by using, respectively, two liters of each of the corresponding test solutions of Example 1, above.

Chicken red blood cells washed in 0.9% saline and then resuspended in 0.9% saline were stringently (rigorously) fixed with formaldehyde/saline solution. In this example, 375 ml of the washed blood cells suspended in two liters of saline were fixed with 540 ml of the formaldehyde/saline solution, for one hour at about 20° to 28° C., then for two hours at about 37° C., and then at about 20° to 28° C. for another 24 hours. The formaldehyde/saline solution was made up in the same proportions as in the above preparation for the human red blood cels. Following the aldehyde treatment, the fixed chicken red cells were washed free of the residual formaldehyde by washing in 0.9% saline.

The above treated human red blood cells in the specified MCV/Alsever's Solutions and the above treated chicken red blood cells (simulated human white blood cells) in 0.9% saline solution were combined to provide three distinct levels of RBC, WBC, MCV and Hgb, namely, normal, low and high levels.

The three levels of RBC, WBC, and MCV were as follows:

| Normal | |
|---|---|
| RBC | $4 \pm 0.5 \times 10^6/mm^3$ |
| WBC | $10 \pm 0.4 \times 10^3/mm^3$ |
| MCV | $85 \pm 3\ \mu^3$ |
| Abnormal - Low | |
| RBC | $3 \pm 0.5 \times 10^6/mm^3$ |
| WBC | $5 \pm 0.4 \times 10^3/mm^3$ |
| MCV | $75 \pm 3\ \mu^3$ |

| -continued | |
| --- | --- |
| Abnormal - High | |
| RBC | $5 \pm 0.5 \times 10^6/mm^3$ |
| WBC | $15 \pm 0.4 \times 10^3/mm^3$ |
| MCV | $95 \pm 3\ \mu^3$ |

The final hematology control products are preferably stored in glass vials or ampules at refrigerated temperatures of about 2° to 8° C. The control products are gently warmed to room temperature (about 15° to 30° C.) prior to use and then applied as control samples in place of the patient's blood specimen in the hematology assay.

In another embodiment of the invention, the hematology control also includes a blood platelet component, preferably human platelets. The platelets also are preferably lightly treated with aldehyde in the same manner as the red blood cell component. Following the aldehyde treatment, the platelets should then be washed with the same modified Alsever's Solution used for washing the corresponding aldehyde treated red blood cell component to provide the desired mean corpuscular volume of the final product. For example, in the hematology control product whose red blood cells are washed with the modified Alsever's Solution to provide a value of $75\mu^3$, the platelets should similarly be washed with the modified Alsever's Solution for the 75 MCV value. An illustrative example of the hematology control containing this blood platelet component is as follows:

EXAMPLE 3

The procedure of Example 2 for treating human red blood cells by washing in saline, lightly contacting with formaldehyde/saline solution and then washing with modified Alsever's Solution is repeated except that: 375 ml of washed human platelets are thus treated instead of 375 ml of washed red blood cells.

The above treated platelets are then combined with the human red blood cell and chicken red blood cell (simulated human white cell) components which had been treated according to the procedure of Example 2 to form the final hematology control product. For a normal hematology control product, the platelets will vary from about 130,000 to about 400,000/mm³. In a typical example of a normal level of RBC, WBC and platelets, the proportions are as follows:

RBC: $4.58 \times 10^6/mm^3$
WBC: $8.00 \times 10^3/mm^3$
Platelets: $200 \times 10^3/mm^3$ Various other examples and modifications of the foregoing examples will be apparent to the person skilled in the art after reading the present disclosure without departing from the spirit and scope of the invention. It is intended that all such further examples be included within the scope of the appended claims.

What is claimed is:

1. A hematology control for mean corpuscular volume determinations comprising an aqueous suspension of mammalian red blood cells in which said red blood cells have been treated to provide a predetermined mean corpuscular volume by contacting with an aqueous aldehyde solution in 0.9% saline in proportions equivalent to about 40 ml of 37% formaldehyde and about 500 ml saline, for about 2 hours at temperature of from about 18° to about 28° C., whereby said red blood cells retain their plasticity for up to about 5 days and then washing said red cells while still retaining said plasticity with Alsever's Solution having a pH of from about 6.8 to about 7.4 and modified to contain from about 0.01% to about 0.21% sodium chloride to provide an osmotic pressure on the cells which is directly proportional to the cell size required for the predetermined mean corpuscular volume.

2. The hematology control of claim 1 in which the predetermined mean corpuscular volume ranges from about 75 to about $95\mu^3$ and the osmotic pressure ranges from about 115 to about 275 milliosmols.

3. The hematology control of claim 1 in which the mammalian red blood cells are human red blood cells.

4. The hematology control of claim 3 including simulated human white blood cells comprising avian red blood cells which have been stringently fixed with dilute aldehyde solution whereby said cells become hard.

5. The hematology control of claim 1 in which the red blood cells are suspended in 0.9% saline solution during said contacting with aldehyde.

6. The hematology control of claim 1 in which the aldehyde is formaldehyde.

7. The hematology control of claim 4 in which the concentration of the human red blood cells ranges from about $3 \times 10^6$ to about $5 \times 10^6/mm^3$ and in which the concentration of the avian red blood cells ranges from about $5 \times 10^3$ to about $15 \times 10^3/mm^3$.

8. A method of making a hematology control having a predetermined mean corpuscular volume comprising treating mammalian red blood cells with an aqueous solution of aldehyde in 0.9% saline solution in proportions equivalent to about 40 ml of 37% formaldehyde and about 500 ml saline, for about 2 hours at temperature of from about 18° to about 28° C., whereby said red cells retain their plasticity for up to about 5 days, adjusting the mean corpuscular volume to any desired level within a range of from about 75 to about $95\mu^3$ by thoroughly washing the red blood cells while still retaining said plasticity in Alsever's Solution having a pH of from about 6.8 to about 7.4 and modified to contain from about 0.01% to about 0.21% sodium chloride to thereby provide an osmotic pressure on the red blood cells of from about 115 to about 275 milliosmols, and thereafter placing the red blood cells in aqueous suspension.

9. The method of claim 8 in which the mammalian red blood cells are human red blood cells.

10. The method of claim 8 in which the aldehyde is formaldehyde.

11. The method of claim 8 in which the pH is about 7.2.

12. The method of claim 8 in which the modified Alsever's Solution contains a sugar component consisting of sucrose having a concentration of about 10 gm per liter.

13. The hematology control of claim 1 including platelets which have been treated with aldehyde and modified Alsever's Solution in the same manner as the red blood cells.

14. The hematology control of claim 3 including human platelets which have been treated with aldehyde and modified Alsever's Solution in the same manner as the red blood cells.

* * * * *